US011648327B2

(12) United States Patent
Nowruzi et al.

(10) Patent No.: US 11,648,327 B2
(45) Date of Patent: May 16, 2023

(54) APPARATUS AND METHOD FOR STERILIZING ENDOSCOPE

(71) Applicant: ASP Global Manufacturing GmbH, Schaffhausen (CH)

(72) Inventors: Keyvan Nowruzi, Mission Viejo, CA (US); Navid Omidbakhsh, Mission Viejo, CA (US)

(73) Assignee: ASP Global Manufacturing GmbH, Schaffhausen (CH)

( * ) Notice: Subject to any disclaimer, the term of this patent is extended or adjusted under 35 U.S.C. 154(b) by 562 days.

(21) Appl. No.: 16/225,035

(22) Filed: Dec. 19, 2018

(65) Prior Publication Data

US 2019/0224356 A1 Jul. 25, 2019

Related U.S. Application Data

(63) Continuation of application No. 15/198,670, filed on Jun. 30, 2016, now Pat. No. 10,314,929.

(51) Int. Cl.
*A61L 2/24* (2006.01)
*A61L 2/18* (2006.01)
(Continued)

(52) U.S. Cl.
CPC .................... *A61L 2/24* (2013.01);
*A61L 2/14* (2013.01); *A61L 2/186* (2013.01);
*A61L 2/20* (2013.01); *A61L 2/202* (2013.01);
*A61L 2/208* (2013.01); *A61L 2/28* (2013.01);
*A61L 2202/11* (2013.01); *A61L 2202/122* (2013.01);
(Continued)

(58) Field of Classification Search
CPC ... A61L 2/24; A61L 2/186; A61L 2/28; A61L 2/14; A61L 2/20; A61L 2/202; A61L 2/208; A61L 2202/122; A61L 2202/18; A61L 2202/11; A61L 2202/14; A61L 2202/24
See application file for complete search history.

(56) References Cited

U.S. PATENT DOCUMENTS 5,527,508 A    6/1996   Childers et al.
5,645,796 A *   7/1997   Caputo ..................... A61L 2/14
                                                                                                                           422/23
(Continued)

FOREIGN PATENT DOCUMENTS

CN        1989893 A     7/2007
CN      101065155 A    10/2007
(Continued)

OTHER PUBLICATIONS

Chinese Office Action and Search Report dated Jun. 3, 2020 for Application No. 201710526246.6, 14 pages.
(Continued)

*Primary Examiner* — Regina M Yoo
(74) *Attorney, Agent, or Firm* — Frost Brown Todd LLP

(57) ABSTRACT

A method of sterilizing an article such as a flexible endoscope is performed in a sterilization chamber. A vacuum is applied in the sterilization chamber while the article is contained in the sterilization chamber. A sterilant is then introduced into the sterilization chamber. The pressure within the sterilization chamber is incrementally increased to provide a step-wise transition from a high vacuum state to atmospheric pressure. The article is thereby sterilized.

31 Claims, 6 Drawing Sheets

(51) Int. Cl.
*A61L 2/28* (2006.01)
*A61L 2/14* (2006.01)
*A61L 2/20* (2006.01)

(52) U.S. Cl.
CPC ....... *A61L 2202/14* (2013.01); *A61L 2202/18* (2013.01); *A61L 2202/24* (2013.01)

(56) References Cited

U.S. PATENT DOCUMENTS

| | | | |
|---|---|---|---|
| 6,030,579 A * | 2/2000 | Addy | A61L 2/14 422/28 |
| 6,325,972 B1 | 12/2001 | Jacobs et al. | |
| 6,365,102 B1 * | 4/2002 | Wu | A61L 2/14 422/23 |
| 6,447,719 B1 | 9/2002 | Agamohamadi et al. | |
| 6,656,426 B1 | 12/2003 | Wang et al. | |
| 6,852,277 B2 | 2/2005 | Platt et al. | |
| 6,852,279 B2 | 2/2005 | Williams et al. | |
| 6,939,519 B2 | 9/2005 | Agamohamadi et al. | |
| 8,012,415 B2 * | 9/2011 | Hanada | A61L 2/14 422/33 |
| 8,230,616 B2 * | 7/2012 | McLaren | A61L 2/208 34/403 |
| 8,366,995 B2 * | 2/2013 | McLaren | A61L 2/24 422/3 |
| 8,882,680 B2 | 11/2014 | Furlong et al. | |
| 9,302,021 B2 | 4/2016 | Klobusnik | |
| 10,314,929 B2 | 6/2019 | Nowruzi et al. | |
| 2006/0280646 A1 | 12/2006 | Shiosawa | |
| 2008/0233002 A1 | 9/2008 | Mizuno et al. | |
| 2011/0076192 A1 | 3/2011 | Robitaille et al. | |
| 2011/0176959 A1 | 7/2011 | Ko | |
| 2013/0236355 A1 * | 9/2013 | Dufresne | A61L 2/208 422/33 |
| 2014/0037495 A1 | 2/2014 | Ahiska et al. | |
| 2015/0064067 A1 | 3/2015 | Klobusnik et al. | |
| 2017/0304477 A1 | 10/2017 | Truong et al. | |
| 2018/0000976 A1 | 1/2018 | Nowruzi et al. | |
| 2020/0230279 A1 | 7/2020 | Nowruzi et al. | |

FOREIGN PATENT DOCUMENTS

| | | | |
|---|---|---|---|
| CN | 103118581 A | 5/2013 | |
| CN | 103747808 A | 4/2014 | |
| CN | 104735893 A | 6/2015 | |
| CN | 105407928 A | 3/2016 | |
| CN | 105709249 A | 6/2016 | |
| EP | 1455843 B1 | 8/2005 | |
| EP | 3041519 B1 | 5/2021 | |
| JP | H11-193010 A | 7/1999 | |
| JP | 2015-223455 A | 12/2015 | |
| WO | WO-2007080907 A1 * | 7/2007 | A61L 2/14 |

OTHER PUBLICATIONS

U.S. Appl. No. 16/843,366, entitled "Apparatus and Method for Sterilizing Endoscope," filed Apr. 8, 2020.
European Search Report and Written Opinion dated Nov. 6, 2017 for Application No. 17178746, 8 pages.
U.S. Appl. No. 62/316,722, filed Apr. 1, 2016.
Japanese Notification of Reasons for Refusal dated Feb. 24, 2021, for Application No. 2017-127176, 7 pages.
Partial International Search Report and Written Opinion dated Sep. 15, 2021, for International Application No. PCT/IB2021/000227, 17 pages.

* cited by examiner

APPARATUS AND METHOD FOR STERILIZING ENDOSCOPE

This application is a continuation of U.S. patent application Ser. No. 15/198,670 filed Jun. 30, 2016, now U.S. Pub. No. 2018/0000976, published Jan. 4, 2018.

BACKGROUND

Re-usable medical devices such as certain surgical instruments, endoscopes, etc., may be sterilized before re-use in order to minimize the likelihood that a contaminated device might be used on a patient, which could cause an infection in the patient. Various sterilization techniques may be employed, such as steam, hydrogen peroxide, peracetic acid, and vapor phase sterilization, either with or without a gas plasma and ethylene oxide (EtO). Each of these methods may depend to a certain extent on the diffusion rates of the sterilization fluids (e.g., gases) upon or into the medical devices to be sterilized.

Before sterilization, medical devices may be packaged within containers or pouches having a semi-permeable barrier that allows transmission of the sterilizing fluid—sometimes referred to as a sterilant—but prevents admission of contaminating organisms, particularly post-sterilization and until the package is opened by medical personnel. For the sterilization cycle to be efficacious, the contaminating organisms within the package must be killed because any organisms that survive the sterilization cycle could multiply and re-contaminate the medical device. Diffusion of the sterilant may be particularly problematic for medical devices that have diffusion-restricted spaces therein because these diffusion-restricted spaces may reduce the likelihood that a sterilization cycle may be effective. For example, some endoscopes have one or more long narrow lumens into which the sterilant must diffuse in sufficient concentration for sufficient time to achieve a successful sterilization cycle.

Sterilization of medical devices may be performed with an automated sterilization system such as a STERRAD® System by Advanced Sterilization Products of Irvine, Calif. Examples of automated sterilization systems are described in U.S. Pat. No. 6,939,519, entitled "Power System for Sterilization Systems Employing Low Frequency. Plasma," issued Sep. 6, 2005, the disclosure of which is incorporated by reference herein; U.S. Pat. No. 6,852,279, entitled "Sterilization with Temperature-Controlled Diffusion Path," issued. Feb. 8, 2005, the disclosure of which is incorporated by reference herein; U.S. Pat. No. 6,852,277, entitled "Sterilization System Employing a Switching Module Adapter to Pulsate the Low Frequency Power Applied to a Plasma," issued Feb. 8, 2005, the disclosure of which is incorporated by reference herein; U.S. Pat. No. 6,447,719, entitled "Power System for Sterilization Systems Employing Low Frequency Plasma," issued Sep. 10, 2002, the disclosure of which is incorporated by reference herein; and U.S. Provisional Pat. App. No. 62/316,722, entitled "System and Method for Sterilizing Medical Devices," filed Apr. 1, 2016, the disclosure of which is incorporated by reference herein.

Some sterilization systems may use vaporized chemical sterilants or chemical gas such as hydrogen peroxide, peracetic acid, ozone, chlorine dioxide, nitrogen dioxide, etc., to sterilize medical devices. Examples of such systems are described in U.S. Pat. No. 6,365,102, entitled "Method of Enhanced Sterilization with Improved Material Compatibility," issued Apr. 2, 2002, the disclosure of which is incorporated by reference herein, and U.S. Pat. No. 6,325,972, entitled "Apparatus and Process for Concentrating a Liquid Sterilant and Sterilizing Articles Therewith," issued Dec. 4, 2001, the disclosure of which is incorporated by reference herein. Some such systems provide a hydrogen peroxide/gas plasma sterilization system comprising a vacuum chamber and plasma source and increased concentration of hydrogen peroxide for sterilization. Some such systems may have difficulty sterilizing lumens of some medical devices if their length exceeds a certain value; or the processing time of such systems may still not be fast enough for some applications. Thus, some medical devices such as long and/or narrow flexible endoscopes may not be completely sterilized by these systems due to the insufficient reach of sterilant vapor to the inside of the channels. Such medical devices might therefore only be disinfected without being sterilized. Sterilization systems that use ethylene oxide may have a relatively long processing time (e.g., longer than 24 hours which may be undesirable in some cases.

Operator error may result in medical devices that are erroneously believed to be decontaminated being returned to service. Confirming that a sterilization cycle has been efficacious may help medical personnel avoid using a contaminated medical device on a patient. The sterilized medical device might not itself be checked for contaminating organisms because such an activity may introduce other contaminating organisms to the medical device, thereby re-contaminating it. Thus, an indirect check may be performed using a sterilization indicator. A sterilization indicator is a device that may be placed alongside or in proximity to a medical device being subject to a sterilization cycle, such that the sterilization indicator is subject to the same sterilization cycle as the medical device. For instance, a biological indictor having a predetermined quantity of microorganisms may be placed into a sterilization chamber alongside a medical device and subject to a sterilization cycle. After the cycle is complete, the microorganisms in the biological indicator may be cultured to determine whether any of the microorganisms survived the cycle. The presence or absence of living microorganisms in the biological indicator will indicate whether the sterilization cycle was effective.

While a variety of systems and methods have been made and used for surgical instrument sterilization, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. OVERVIEW OF EXEMPLARY STERILIZATION SYSTEM

Figure 1:
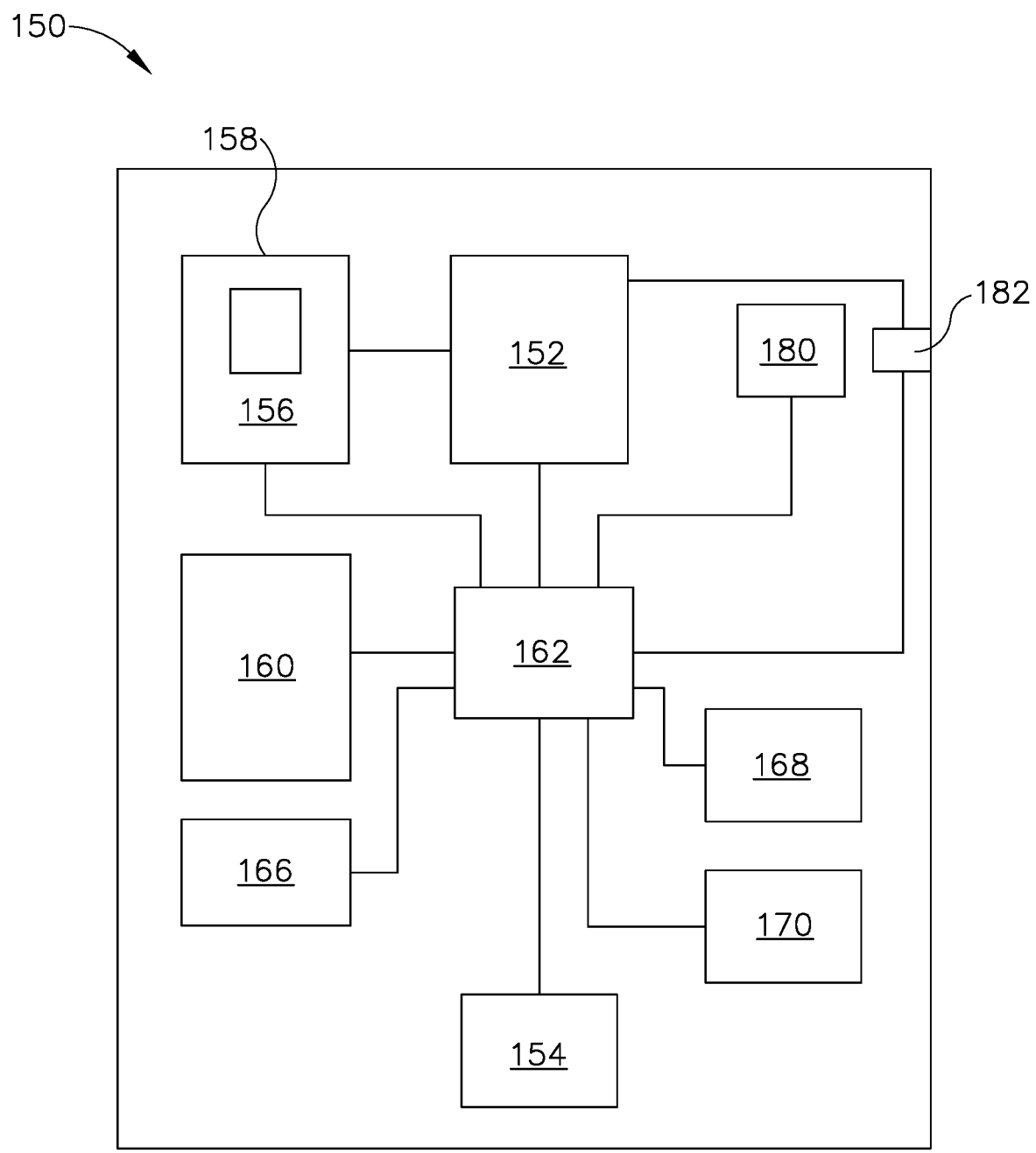
FIG. 1 depicts a schematic view of an exemplary medical device sterilizing cabinet.

FIG. 1 depicts an exemplary sterilizing cabinet (150) that is operable to sterilize medical devices such as endoscopes, etc. Sterilizing cabinet (150) of the present example includes a sterilization chamber (152), which is configured to receive one or more medical devices for sterilization. While not shown, sterilizing cabinet (150) also includes a door that opens and closes sterilization chamber (152) in response to actuation of a kick plate. An operator may thereby open and close sterilization chamber (152) in a hands-free fashion. Of course, any other suitable features may be used to provide selective access to sterilization chamber. Sterilizing cabinet (150) also includes a sterilization module (156) that is operable to dispense a sterilant into sterilization chamber (152) in order to sterilize medical devices contained in sterilization chamber (152). In the present example, sterilization module (156) is configured to receive replaceable sterilant cartridges (158) containing a certain amount of sterilant. By way of example only, each sterilant cartridge (158) may contain enough sterilant to perform five sterilization procedures.

Sterilizing cabinet (150) of the present example further includes a touch screen display (160). Touch screen display (160) is operable to render the various user interface display screens, such as those described in U.S. Provisional Pat. App. No. 62/316,722, the disclosure of which is incorporated by reference herein. Of course, touch screen display (160) may display various other screens as well. Touch screen display (160) is further configured to receive user input in the form of the user contacting touch screen display (160) in accordance with conventional touch screen technology. In addition, or in the alternative, sterilizing cabinet (150) may include various other kinds of user input features, including but not limited to buttons, keypads, keyboards, a mouse, a trackball, etc.

Sterilizing cabinet (150) of the present example further includes a processor (162), which is in communication with sterilization module (156) and with touch screen display (160). Processor (162) is operable to execute control algorithms to drive sterilization module (156) in accordance with user input. Processor (162) is further operable to execute instructions to display the various screens on touch screen display (160); and to process instructions received from a user via touch screen display (160) (and/or via other user input features). Processor (162) is also in communication with various other components of sterilization cabinet (150) and is thereby operable to drive those components and/or process input and/or other data from those components. Various suitable components and configurations that may be used to form processor (162) will be apparent to those of ordinary skill in the art in view of the teachings herein.

Sterilizing cabinet (150) of the present example further includes an identification tag reader (166), which is operable to read an identification tag of a biological indicator as described herein. By way of example only, identification tag reader (166) may comprise an optical reader that is operable to read an optical identification tag (e.g., barcode, QR code, etc.) of a biological indicator. In addition; or in the alternative, identification tag reader (166) may comprise MD reader that is operable to read an RFID identification tag (e.g., barcode, QR code, etc.) of a biological indicator. Various suitable components and configurations that may be used to form identification tag reader (166) will be apparent to those of ordinary skill in the art in view of the teachings herein. Data received through identification tag reader (166) is processed through processor (162).

Sterilizing cabinet (150) of the present example further includes a memory (168), which is operable to store control logic and instructions and that are executed by processor (162) to drive components such as sterilization module (156), touch screen display (160), communication module (154), and identification tag reader (166). Memory (168) may also be used to store results associated with setup of a sterilization cycle, performance of a load conditioning cycle, performance of a sterilization cycle, and/or various other kinds of information. Various suitable forms that memory (168) may take, as well as various ways in which memory (168) may be used, will be apparent to those of ordinary skill in the art in view of the teachings herein.

Sterilizing cabinet (150) of the present example further includes a printer (170), which is operable to print information such as results associated with setup of a sterilization cycle, performance of a load conditioning cycle, performance of a sterilization cycle, and/or various other kinds of information. By way of example only, printer (170) may comprise a thermal printer, though of course any other suitable kind of printer may be used. Various suitable forms that printer (170) may take, as well as various ways in which printer (170) may be used, will be apparent to those of ordinary skill in the art in view of the teachings herein. It should also be understood that printer (170) is merely optional and may be omitted in some versions.

Sterilizing cabinet (150) of the present example further includes a vacuum source (180) and a venting valve (182). Vacuum source (180) is in fluid communication with sterilization chamber (152) and is also in communication with processor (162). Thus, processor (162) is operable to selectively activate vacuum source (180) in accordance with one or more control algorithms. When vacuum source (180) is activated, vacuum source (180) is operable to reduce the pressure within sterilization chamber (152) as will be described in greater detail below. Venting valve (182) is also in fluid communication with sterilization chamber (152). In addition, venting valve (182) is in communication with processor (162) such that processor (162) is operable to selectively activate venting valve (182) in accordance with one or more control algorithms. When venting valve (182) is activated, venting valve (182) is operable to vent sterilization chamber (152) to atmosphere as will be described in greater detail below. Various suitable components that may be used to provide vacuum source (180) and venting valve (182) will be apparent to those of ordinary skill in the art in view of the teachings herein.

In addition to the foregoing, sterilizing cabinet (150) may be configured and operable in accordance with at least some of the teachings of U.S. Pat. No. 6,939,519, the disclosure of which is incorporated by reference herein; U.S. Pat. No. 6,852,279, the disclosure of which is incorporated by reference herein; U.S. Pat. No. 6,852,277, the disclosure of which is incorporated by reference herein; U.S. Pat. No. 6,447,719, the disclosure of which is incorporated by reference herein; U.S. Pat. No. 6,365,102, the disclosure of which is incorporated by reference herein; U.S. Pat. No. 6,325,972, the disclosure of which is incorporated by reference herein; and/or U.S. Provisional Patent App. No. 62/316,722, the disclosure of which is incorporated by reference herein.

II. OVERVIEW OF EXEMPLARY STERILIZATION PROCESS

Figure 2:
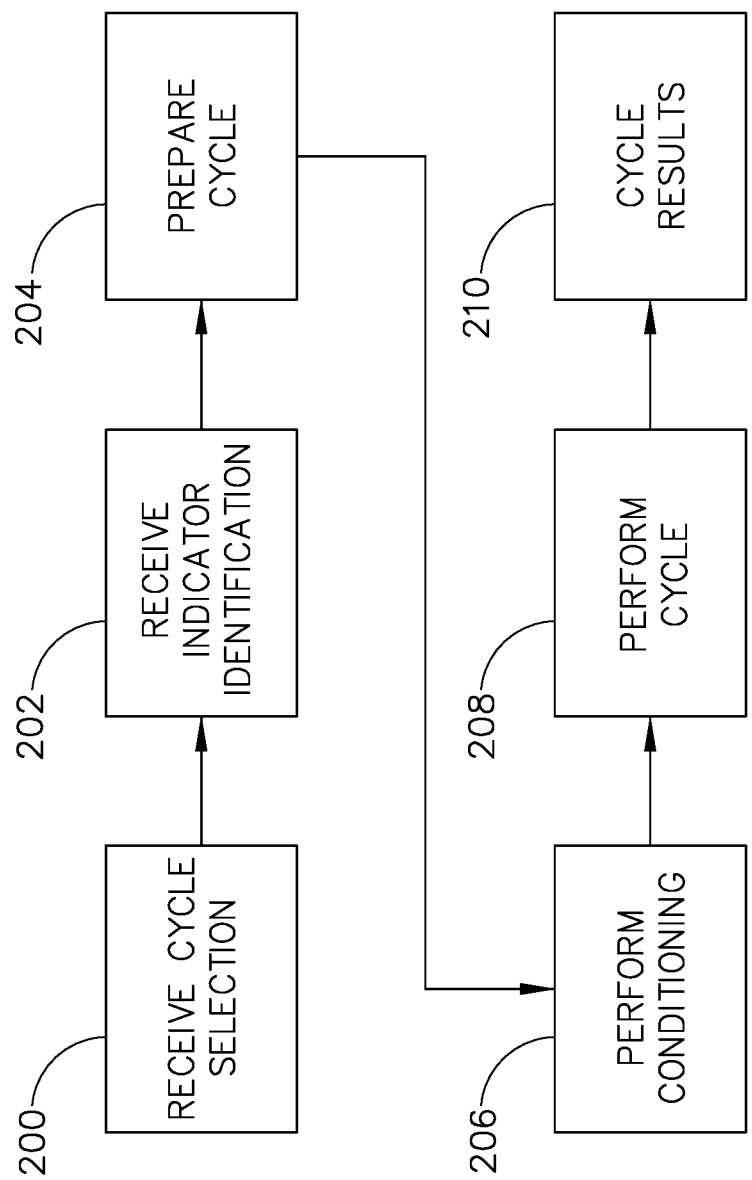
FIG. 2 depicts a high level flowchart of an exemplary set of steps that a sterilizing cabinet of the system of FIG. 1 could perform to sterilize a medical device.

FIG. 2 depicts a high level flowchart of an exemplary set of steps that sterilizing cabinet (150) could perform to sterilize a used medical device, such as an endoscope. Sterilizing cabinet (150) may be configured to perform one or more sterilization cycles, with different sterilization cycles being appropriate for different types and quantities of medical devices. Thus, as an initial step, sterilizing cabinet (150) may display one or more available sterilization cycles via touch screen display (160) and then receive a sterilization cycle selection (block 200) from the user.

Sterilizing cabinet (150) may also display instructions indicating whether a biological indicator should be used with the selected sterilization cycle, and receive a biological indicator identification (block 202). Such a biological indicator identification (block 202) may be provided via identification tag reader (166), via touch screen display (160), or otherwise. A biological indicator may be placed inside sterilization chamber (152) of sterilizing cabinet (150) before the sterilization cycle begins and may remain in the sterilization chamber during the sterilization cycle. The user may thus identify the particular biological indicator (block 202) before the biological indicator is placed in the sterilization chamber. The biological indicator may contain microorganisms that are responsive to a particular sterilization cycle. Upon completion of the sterilization cycle, the biological indicator may be tested for the microorganisms in order to provide a measure of the effectiveness of the sterilization cycle. A biological indicator may not necessarily be required for all sterilization cycles, but may be required based on hospital rules or local regulations.

Selection of a sterilization cycle (block 200) and identification of a biological indicator (block 202) may define one or more requirements for the configuration and arrangement of medical devices within sterilization chamber (152). Thus, in order to provide preparation for the sterilization cycle (204) once the sterilization cycle has been selected (block 200) and the biological indicator has been identified (block 202), sterilizing cabinet (150) may provide a display via touch screen display (160) indicating a proper medical device placement. This display may serve as a visual guide to a user's placement of medical device(s) (and perhaps a biological indicator) within sterilizing chamber (152) of sterilizing cabinet (150), based on the sterilization cycle selection (block 200). A door of sterilization chamber (152) may be opened to enable the user to place the medical device(s) (and perhaps a biological indicator) within sterilizing chamber (152) as instructed.

Once the user has placed the medical device in sterilizing chamber (152) based on these instructions, the user may press a start button or other button indicating that medical device placement is complete. In some versions, sterilizing cabinet (150) is configured to automatically verify proper medical device placement. By way of example only, sterilizing cabinet (150) may employ photo sensors, imaging devices, weight sensors, and/or other components to verify proper medical device placement in sterilizing chamber (152). It should be understood, however, that some versions of sterilizing cabinet (150) may lack the capability of automatically verifying proper placement of a medical device within sterilizing chamber (152).

If medical device placement is verified and/or the user has otherwise completed the cycle preparation (block 204), sterilizing cabinet (150) may start a load conditioning process (block 206). The load conditioning process (block 206) prepares sterilization chamber (152) and the medical device(s) within sterilization chamber (152) for optimal sterilization during a sterilization cycle. Conditioning may include controlling and optimizing one or more characteristics of sterilization chamber (152). For example, during load conditioning, sterilizing cabinet (150) may continuously monitor the level of moisture within sterilization chamber (152) while reducing the level of moisture by, for example, circulating and dehumidifying the air of sterilization chamber (152), creating a vacuum within sterilization chamber (152), heating sterilization chamber (152), and/or other methods for dehumidifying a sealed chamber. This may continue until sterilizing cabinet (150) determines that an acceptable level of moisture has been reached.

As part of the load conditioning cycle (block 206), sterilizing cabinet (150) may also continuously detect the temperature within sterilization chamber (152) while heating sterilization chamber (152) by, for example, convection of heated air, conduction through an interior surface of sterilization chamber (152), and/or using other techniques. This may continue until sterilizing cabinet (150) determines that an acceptable internal temperature has been reached. Various conditioning actions such as controlling temperature or humidity may be performed in parallel or in sequence. It should also be understood that the load conditioning cycle (block 206) may verify that the sterilization chamber is sealed; verifying contents of the sterilization chamber; checking physical characteristics of the contents of the sterilization chamber such as content volume, content weight, or other characteristics; and/or performing one or more conditioning steps that may include chemical treatment, plasma treatment, or other types of treatment to reduce moisture, raise temperature, and/or otherwise prepare the medical devices in sterilization chamber (1 for the sterilization cycle (block 208).

While the one or more conditioning actions are being performed as part of the load conditioning cycle (block 206), sterilizing cabinet (150) may display information via touch screen display (160) indicating to a user the duration of time before the sterilization cycle (block 208) performance may begin. Once all load conditioning criteria have been successfully met, the load conditioning cycle (block 206) is complete, and the sterilization cycle (block 208) may then be performed, it should therefore be understood that sterilizing cabinet (150) is configured such that the sterilization cycle (block 208) is not actually initiated until after the load conditioning cycle (block 206) is complete. It should also be understood that the load conditioning cycle (block 206) may be omitted or varied in some versions of sterilizing cabinet (150) operation.

As noted above, sterilization cabinet (150) may begin performing the sterilization cycle (block 208) automatically and immediately after load conditioning (block 206) has been completed. The sterilization cycle (block 208) may include exposing the medical device(s) in the sterilizing chamber to pressurized sterilant gas, further heat treatment, chemical treatment, plasma treatment, vacuum treatment, and/or other types of sterilization procedures. During performance of the sterilization cycle (block 208), sterilization cabinet (150) may display information via touch screen display (160) such as a duration remaining for the sterilization cycle (block 208), the current stage of the sterilization cycle (block 208) (e.g. plasma, vacuum, injection, heat, chemical treatment), and/or other information.

Figure 3:
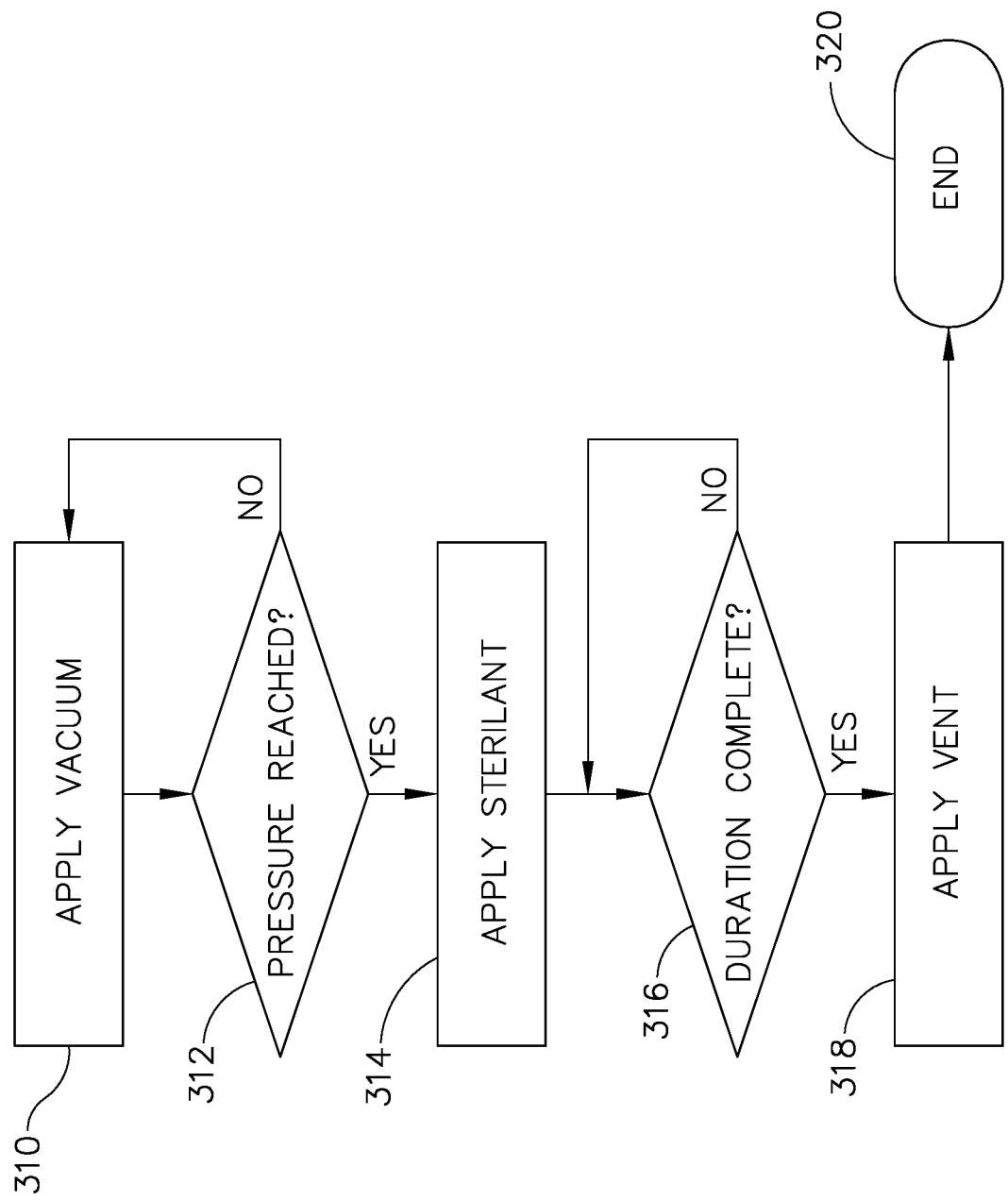
FIG. 3 depicts a flowchart of an exemplary set of steps that may be carried out as part of a sterilization cycle within the set of steps of FIG. 2.

In some versions, the sterilization cycle (block 208) includes the exemplary sub-steps shown in FIG. 3. In particular, the cycle may begin with a vacuum being applied (block 310) within sterilization chamber (152). In order to provide such a vacuum, processor (162) may activate vacuum source (180) in accordance with a control algorithm. Processor (162) will then determine (block 312) whether a sufficient pressure level has been reached within sterilization chamber (152). By way of example only, processor (162) may monitor data from one or more pressure sensors within sterilization chamber (152) as part of the determination step (block 312). Alternatively, processor (162) may simply activate vacuum source (180) for a predetermined time period and assume that the appropriate pressure has been reached in sterilization (152) based upon the duration for which vacuum source (180) is activated. Other suitable ways in which processor (162) may determine (block 312) whether a sufficient pressure level has been reached within sterilization chamber (152) will be apparent to those of ordinary skill in the art in view of the teachings herein. Until the appropriate pressure level has been reached within sterilization chamber (152), vacuum source (180) will remain activated.

Once sterilization chamber (152) reaches an appropriate pressure level (e.g., between approximately 0.2 torr and approximately 10 torr), processor (162) then activates sterilization module (156) to apply a sterilant (block 314) in sterilization chamber (152). This stage of the process may be referred to as the "transfer phase." By way of example only, the sterilant may comprise a vapor of oxidizing agent such as hydrogen peroxide, peroxy acids (e.g. peracetic acid, performic acid, etc.), ozone, or a mixture thereof. Furthermore, the sterilant may comprise chlorine dioxide. Various other suitable forms that the sterilant may take are described herein; while other forms will be apparent to those of ordinary skill in the art in view of the teachings herein. It should also be understood that, in some versions, the sterilant may be applied (block 314) in different ways based on the user's selection of cycle (block 200) as described above. Once the sterilant has been applied (block 314) to sterilization chamber (152), processor (162) monitors the time (block 316) to determine whether a sufficient, predetermined duration has passed. By way of example only, this predetermined duration may be anywhere from a few seconds to several minutes. Until the predetermined duration has passed, sterilization chamber (152) remains in a sealed state at the above-noted predetermined pressure level, with the applied sterilant acting upon the medical device(s) contained within sterilization chamber (152).

After the predetermined duration has passed, processor (162) activates (block 318) venting valve (182) to vent sterilization chamber (152) to atmosphere. In some versions, sterilization chamber (152) is allowed to reach atmospheric pressure, while in other versions sterilization chamber (152) only reaches sub-atmospheric pressure. The venting stage of the process may be referred to as the "diffusion phase." In the present example, the sterilization cycle is then complete (block 320) after completion of the diffusion phase. In some other instances, vacuum is again applied to sterilization chamber (152) after completion of the diffusion phase; and then a plasma is applied to sterilization chamber (152). It should be understood that the entire sterilization cycle shown in FIG. 3 (including the above-noted variation where a subsequent vacuum then sterilization are applied) may be repeated one or more times after being completed once. In other words, a medical device may remain within sterilization chamber (152) and experience two or more iterations of the entire cycle shown in FIG. 3 (including the above-noted variation where a subsequent vacuum then sterilization are applied). The number of iterations may vary based on the cycle selection (block 200), which may be influenced by the particular kind of medical device that is being sterilized in sterilization chamber (152).

Figure 4:
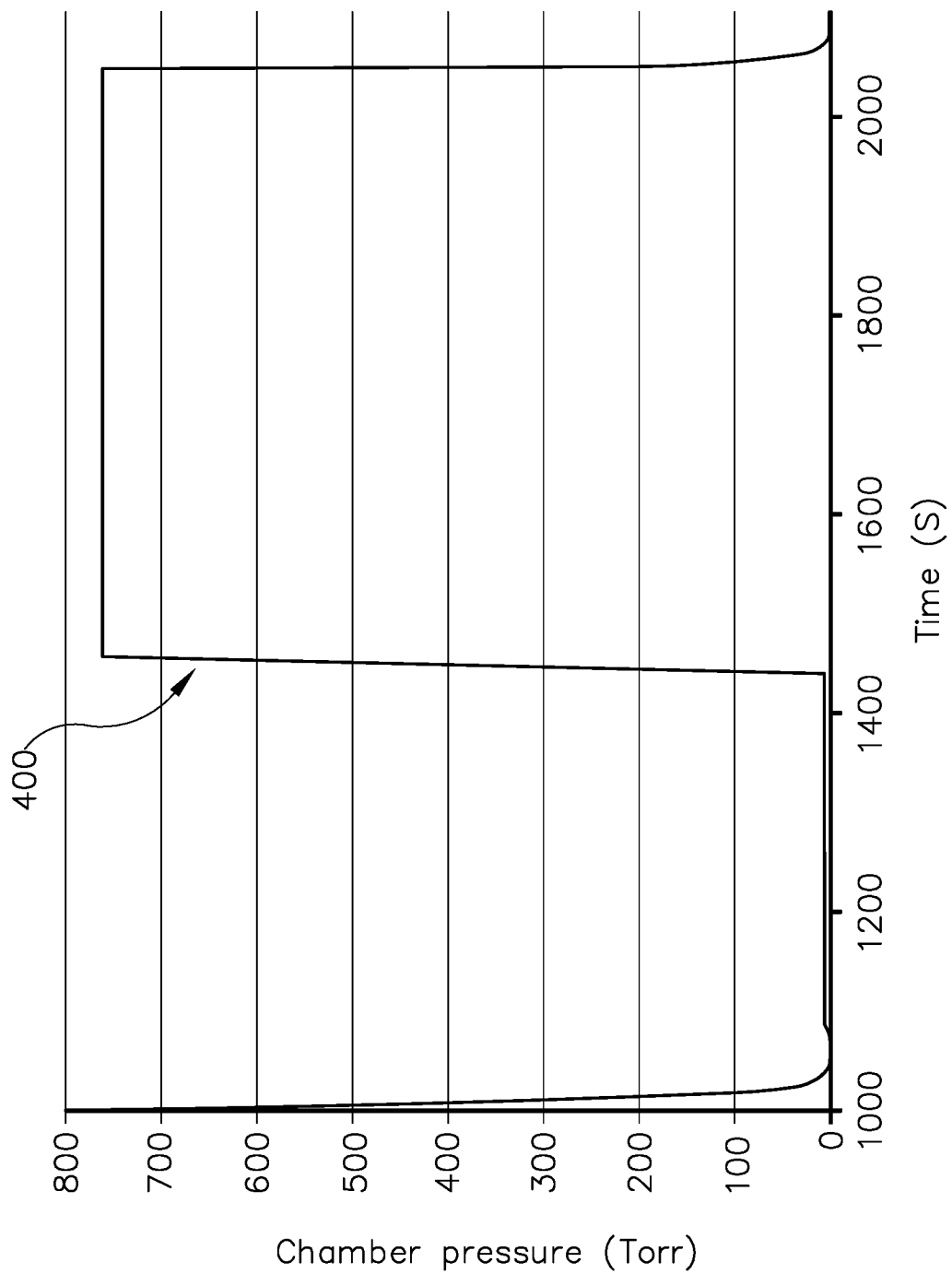
FIG. 4 depicts a graph showing an exemplary plot of vacuum pressure in a sterilization chamber of the sterilizing cabinet of FIG. 1 over time during performance of the sterilization cycle of FIG. 3.

FIG. 4 depicts an exemplary plot (400) showing the pressure within sterilization chamber (152) during performance of the sterilization cycle (block 208) as depicted in FIG. 3 and as described above. As can be seen, the pressure level drops significantly and suddenly when vacuum source (180) is activated to apply vacuum (block 310) to sterilization chamber (152). The pressure level then stays substantially constant while the sterilant is applied (block 314) and during the subsequent, predetermined duration (block 316). The pressure level then increases significantly and suddenly when venting valve (182) is activated (block 318) to vent sterilization chamber (152) to atmosphere. Thus, in general terms, plot (400) shows how the pressure within sterilization chamber (152) simply toggles between a single relatively high level (i.e., atmospheric pressure) and a single relatively low level (i.e., a vacuum state). An exemplary alternative sterilization cycle is described in greater detail below with reference to FIGS. 5-6.

Upon completion of the sterilization cycle (block 208), sterilization cabinet (150) may cycle the results (block 210) of the sterilization cycle (block 208). For instance, if the sterilization cycle (block 208) was canceled or unable to complete due to error or by a user action, sterilizing cabinet (150) may remain sealed and may also display a sterilization cycle cancellation message via touch screen display (160); as well as various details relating to the sterilization cycle, such as date, time, configuration, elapsed time, sterilization cycle operator, the stage at which the sterilization cycle failed, and other information that may be used to identify why the sterilization cycle. If the sterilization cycle (block 208) is completed successfully, sterilization cabinet (150) may display a notification via touch screen display (160) indicating successful completion of the sterilization cycle (block 208). In addition, sterilization cabinet (150) may display information such as sterilization cycle identifier, sterilization cycle type, start time, duration, operator, and other information (666).

In addition to the foregoing, sterilizing cabinet (150) may be configured to perform sterilization processes in accordance with at least some of the teachings of U.S. Pat. No. 6,939,519, the disclosure of which is incorporated by reference herein; U.S. Pat. No. 6,852,279, the disclosure of which is incorporated by reference herein; U.S. Pat. No. 6,852,277, the disclosure of which is incorporated by reference herein; U.S. Pat. No. 6,447,719, the disclosure of which is incorporated by reference herein; U.S. Pat. No. 6,365,102, the disclosure of which is incorporated by reference herein; U.S. Pat. No. 6,325,972, the disclosure of which is incorporated by reference herein; and/or U.S. Provisional Patent App. No. 62/316,722, the disclosure of which is incorporated by reference herein.

III. EXEMPLARY ALTERNATIVE STERILIZATION CYCLE

As noted above, some versions of sterilizing cabinet (150) may have difficulty effectively sterilizing medical devices such as flexible endoscopes with relatively long, narrow lumens. For instance, some conventional sterilizing cabinets may be capable of sterilizing lumens that are shorter than or equal to approximately 875 mm, with a lumen diameter of approximately 1 mm or larger. It may therefore be desirable to provide a modified sterilization cycle (block 208) that further promotes effective sterilization of a medical device having one or more relatively long, narrow lumens. A merely illustrative example of such a modified sterilization cycle is described in greater detail below. By way of example only, a medical device having one or more relatively long, narrow lumens may comprise a gastrointestinal endoscope that is between approximately 1 m long and approximately 3 m long, with a lumen having a diameter between approximately 0.5 mm and approximately 2.0 mm. It should nevertheless be understood that the process described below may also be performed on endoscopes having a length of at least approximately 500 mm or at least approximately 800 mm, with a lumen having a diameter less than approximately 6.0 mm.

Figure 5:
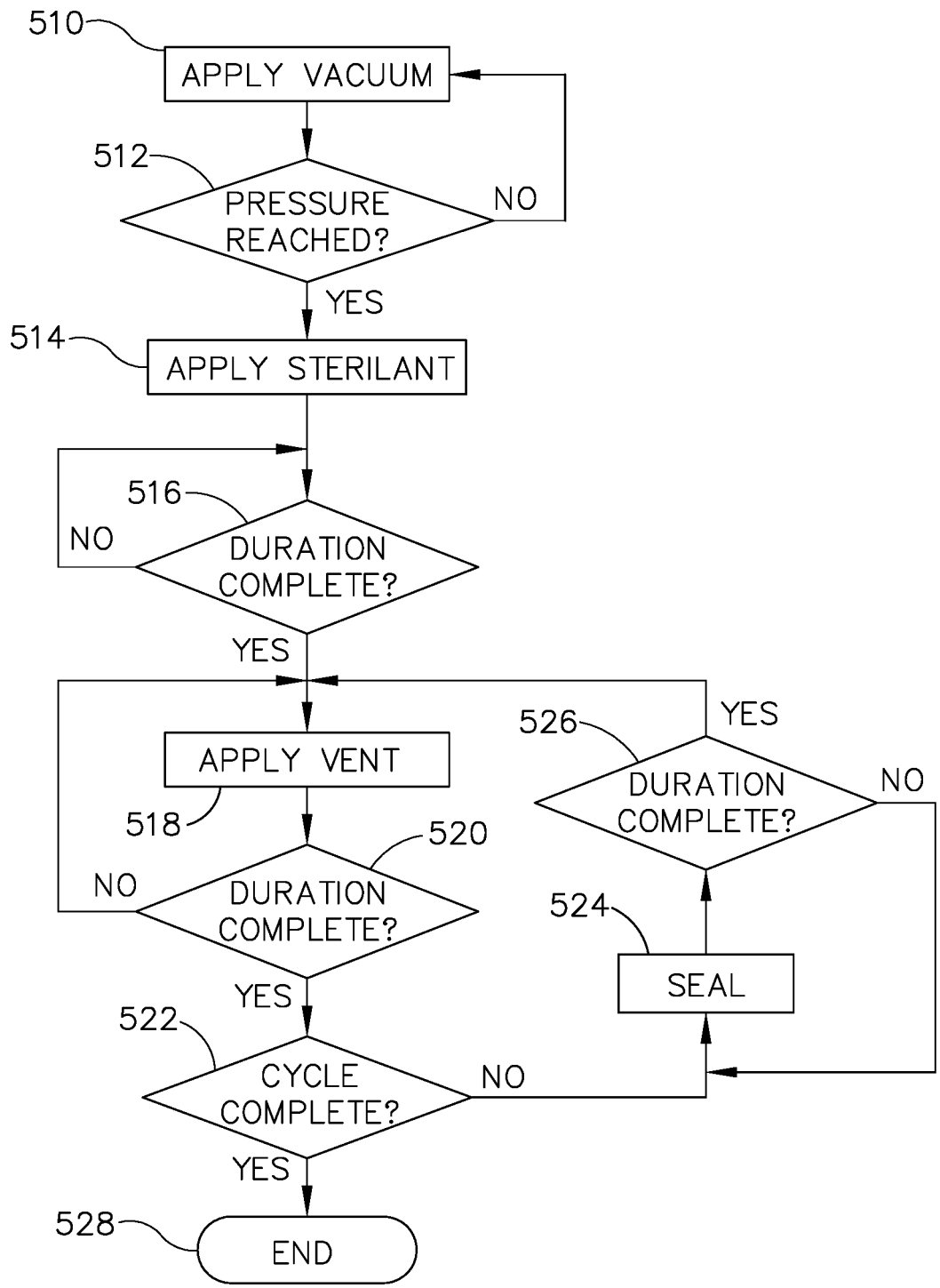
FIG. 5 depicts a flowchart of an exemplary alternative set of steps that may be carried out as part of a sterilization cycle within the set of steps of FIG. 2.

FIG. 5 depicts an exemplary alternative set of sub-steps that may be performed to provide the sterilization cycle (block 208) of sterilizing cabinet (150). In particular, the cycle may begin with a vacuum being applied (block 510) within sterilization chamber (152). In order to provide such a vacuum; processor (162) may activate vacuum source (180) in accordance with a control algorithm. Processor (162) will then determine (block 512) whether a sufficient pressure level has been reached within sterilization chamber (152). By way of example only, processor (162) may monitor data from one or more pressure sensors within sterilization chamber (152) as part of the determination step (block 512). Alternatively, processor (162) may simply activate vacuum source (180) for a predetermined time period and assume that the appropriate pressure has been reached in sterilization (152) based upon the duration for which vacuum source (180) is activated. Other suitable ways in which processor (162) may determine (block 512) whether a sufficient pressure level has been reached within sterilization chamber (152) will be apparent to those of ordinary skill in the art in view of the teachings herein. Until the appropriate pressure level has been reached within sterilization chamber (152), vacuum source (180) will remain activated.

Once sterilization chamber (152) reaches an appropriate pressure level (e.g., between approximately 0.2 torr and approximately 10 torr), processor (162) then activates sterilization module (156) to apply a sterilant (block 514) in sterilization chamber (152). By way of example only, the sterilant may comprise a vapor of oxidizing agent such as hydrogen peroxide, peroxy acids (e.g. peracetic acid, performic acid, etc.), ozone, or a mixture thereof. Furthermore, the sterilant may comprise chlorine dioxide or nitrogen dioxide. Various other suitable forms that the sterilant may take are described herein; while other forms will be apparent to those of ordinary skill in the art in view of the teachings herein. It should also be understood that, in some versions, the sterilant may be applied (block 514) in different ways based on the user's selection of cycle (block 200) as described above. Once the sterilant has been applied (block 514) to sterilization chamber (152), processor (162) monitors the time (block 516) to determine whether a sufficient, predetermined duration has passed. By way of example only, this predetermined duration may be anywhere from a few seconds to several minutes. Until the predetermined duration has passed, sterilization chamber (152) remains in a sealed state at the above-noted predetermined pressure level, with the applied sterilant acting upon the medical device(s) contained within sterilization chamber (152). This stage of the process may be referred to as the "transfer phase."

After the predetermined duration has passed, processor (162) activates (block 518) venting valve (182) to vent sterilization chamber (152) to atmosphere. With sterilization chamber (152) being vented (block 518) to atmosphere, processor (162) monitors the time (block 520) to determine whether a sufficient, predetermined venting (block 518) duration has passed. Until the predetermined venting (block 518) duration has passed, sterilization chamber (152) remains in a vented state. After the predetermined venting (block 518) duration has passed, processor (162) determines (block 522) whether the sterilization cycle is complete. Examples of how this determination (block 522) may be made will be described in greater detail below. It should be understood that, in the present example, the predetermined venting (block 518) duration may be very brief. By way of example only, the predetermined venting (block 518) duration may be approximately one second, two seconds, three seconds, four seconds, five seconds, or any other suitable duration.

If processor (162) determines (block 522) that the sterilization cycle is complete, then the sterilization cycle is in fact complete (block 528). However, if processor (162) determines (block 522) that the sterilization cycle is not yet complete, then processor (162) closes venting valve (182) to seal (block 524) sterilization chamber (152) at a pressure level that is still less than atmospheric pressure. As noted above, the venting (block 518) duration is very short in this example, such that the act of sealing (block 524) may occur very quickly after venting (block 518) is initiated, assuming that the determinations (block 520, 522) confirm that sealing (block 524) is in order.

Sterilization chamber (152) will remain sealed (block 524) for a certain period of time. In particular, with sterilization chamber (152) being sealed (block 524), processor (162) monitors the time (block 526) to determine whether a sufficient, predetermined sealing (block 524) duration has passed. Until the predetermined sealing (block 524) duration has passed, sterilization chamber (152) remains in a sealed state. After the predetermined sealing (block 524) duration has passed, processor (162) activates (block 518) venting valve (182) again to vent sterilization chamber (152) to atmosphere. By way of example only, the predetermined sealing duration may be between approximately 5 seconds and 5 minutes, or more particularly between approximately 10 seconds and approximately 2 minutes, or more particularly between approximately 20 seconds and approximately 2 minutes.

At this point the process continues through the steps (blocks 518, 520, 522, 524, 526) described above, such that the process provides a series of venting (block 518) and sealing (block 524) of sterilization chamber (152), allowing the pressure within sterilization chamber (152) to increase in a stepwise fashion until sterilization chamber (152) reaches atmospheric pressure or some predetermined sub-atmospheric pressure. Again, each step of venting (block 518) is very brief in this example, such that the pressure of sterilization chamber (152) is held at levels below atmospheric pressure during the acts of sealing (block 524) (e.g., for a duration between approximately a few seconds or a few minutes). By way of example only, until the final step of venting (block 518) is reached, each step of venting (block 518) may result in a respective increase in the pressure within sterilization chamber (152) by approximately 10 torr to approximately 100 torr, or more particularly by approximately 10 torr to approximately 30 torr. Other suitable step-wise pressure increase values will be apparent to those of ordinary skill in the art in view of the teachings herein. Once sterilization cabinet (150) reaches the end of the process, venting valve (182) remains open to allow sterilization chamber (152) to remain at atmospheric pressure. The final venting step (block 518) of the process may be referred to as the "diffusion phase."

In some versions, the venting duration (block 520) and/or the sealing duration (block 526) may vary. For instance, the venting duration (block 520) and/or the sealing duration (block 526) may vary based on the cycle selection (block 200), which may be influenced by the particular kind of medical device that is being sterilized in sterilization chamber (152). In addition, or in the alternative, the venting duration (block 520) and/or the sealing duration (block 526) may vary based on where the sterilization cycle is at in the process (i.e., which venting (block 518) iteration and/or which sealing (block 524) iteration). Various suitable ways in which the venting duration (block 520) and/or the sealing duration (block 526) may vary, and various bases upon which such durations may vary, will be apparent to those of ordinary skill in the art in view of the teachings herein.

Figure 6:
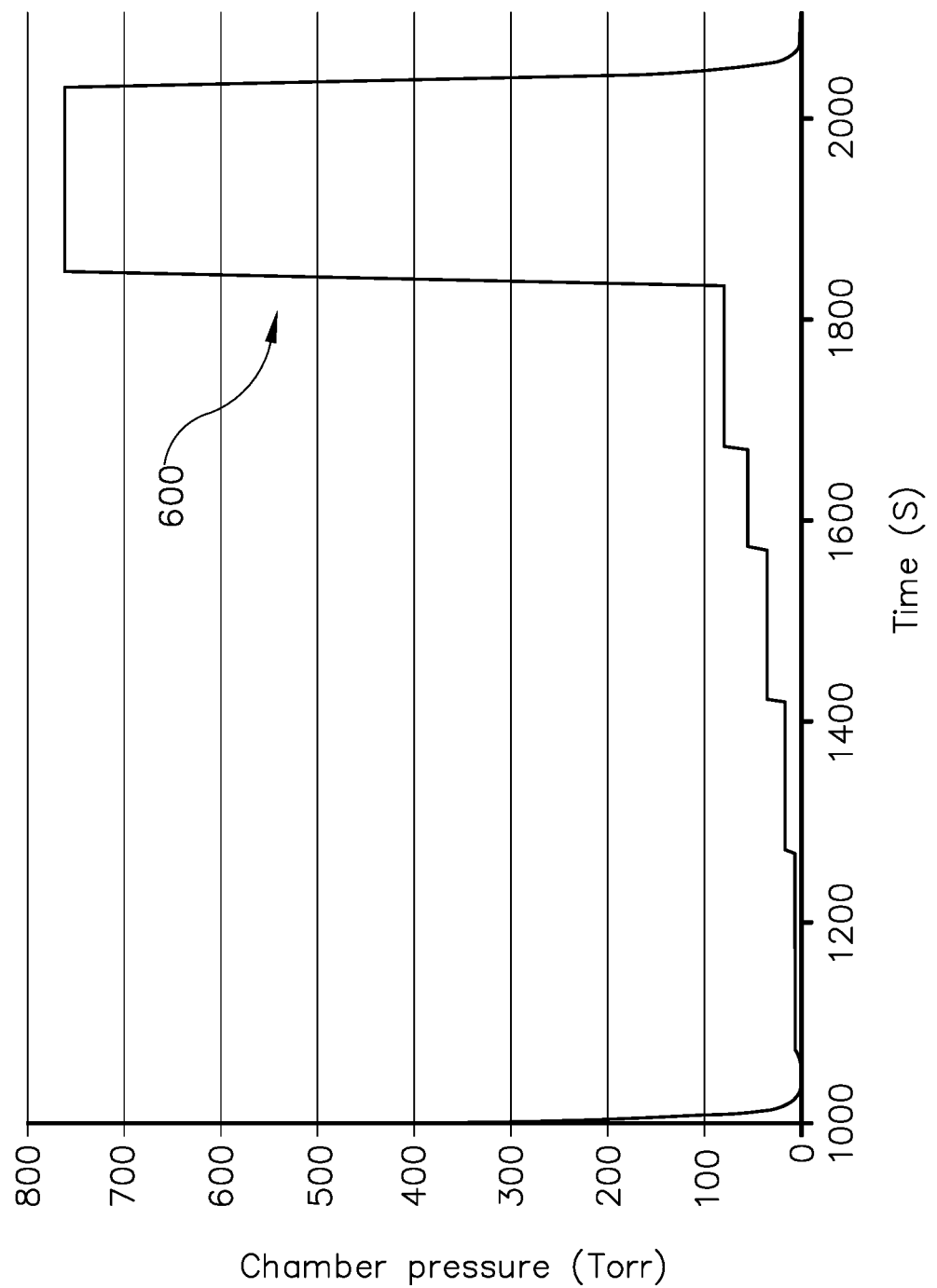
FIG. 6 depicts a graph showing another exemplary plot of vacuum pressure in a sterilization chamber of the sterilizing cabinet of FIG. 1 over time during performance of the sterilization cycle of FIG. 5.

FIG. 6 depicts an exemplary plot (600) showing the pressure within sterilization chamber (152) during performance of the sterilization cycle (block 208) as depicted in FIG. 5 and as described above. As can be seen, the pressure level drops significantly and suddenly when vacuum source (180) is activated to apply vacuum (block 510) to sterilization chamber (152). The pressure level then stays substantially constant while the sterilant is applied (block 514) and during the subsequent, predetermined duration (block 516). The pressure level then increases slightly when venting valve (182) is activated (block 518) to vent sterilization chamber (152) to atmosphere; yet stays at a level below atmosphere when sterilization chamber (152) is sealed (block 524). The pressure level then again increases slightly when venting valve (182) is again activated (block 518) to vent sterilization chamber (152) to atmosphere; yet still stays at a level below atmosphere when sterilization chamber (152) is again sealed (block 524).

In the example shown in FIG. 6, the cycle provides four iterations of brief venting (block 518), followed by four iterations of sealing (block 524), before finally venting (black 518) fully to atmosphere. Thus, in general terms, plot (600) shows how the pressure within sterilization chamber (152) is increased in a step-wise fashion from a substantial vacuum state to atmospheric pressure. While FIG. 6 shows four iterations of brief venting and brief sealing, other processes may employ any other suitable number of iterations of brief venting and brief sealing. By way of example only, variations may provide anywhere between two iterations of brief venting and brief sealing and 100 iterations of brief venting and brief sealing, or more particularly between two iterations of brief venting and brief sealing and ten iterations of brief venting and brief sealing, or more particularly between three iterations of brief venting and brief sealing and seven iterations of brief venting and brief sealing.

In some instances, the process shown in FIGS. 5-6 may provide more effective sterilization of some medical devices as compared to the sterilization of the same medical devices using the process shown in FIGS. 3-4. In particular, and without being limited by theory, the step-wise venting of sterilization chamber (152) may provide agitation of the contents of sterilization chamber (152), which may assist in driving the sterilant into the lumen(s) and/or other internal spaces within the medical device. Moreover, and again without being limited by theory, the step-wise venting of sterilization chamber (152) associated with the process shown in FIGS. 5-6 may provide convective mass transfer of sterilant vapor molecules inside the lumen(s) and/or other internal spaces within the medical device; as compared to the simple diffusive mass transfer of vapor associated with the process shown in FIGS. 3-4. Thus, when sterilization cabinet (150) performs the process shown in FIGS. 5-6, sterilization cabinet (150) may sterilize a relatively long gastrointestinal endoscope (e.g., up to approximately 3 m in length and with a lumen having a diameter up to approximately 1 mm); as compared to sterilization cabinet (150) performing the process shown in FIGS. 3-4, which would not be able to sterilize the long, narrow lumens of the same kind of gastrointestinal endoscope.

It should also be understood that the entire cycle shown in FIGS. 5-6 may be repeated one or more times after being completed once. In other words, a medical device may remain within sterilization chamber (152) and experience two or more iterations of the entire cycle shown in FIGS. 5-6. The number of iterations may vary based on the cycle selection (block 200), which may be influenced by the particular kind of medical device that is being sterilized in sterilization chamber (152).

By way of example only, an endoscope with a 3 m long lumen may be placed in sterilization chamber (152). Vacuum may be applied (block 510) to achieve a pressure level of approximately 4.5 torr in sterilization chamber (152). Sterilant (e.g., approximately 1 mL of a hydrogen peroxide vapor at a concentration of 59%) may then be applied (block 514) to provide a transfer phase lasting approximately 30 seconds. Sterilization chamber (152) may then be briefly vented (block 518) to achieve a pressure level of approximately 13.7 torr, and then sterilization chamber (152) may be sealed (block 524). Sterilization chamber (152) may be held at the approximately 13.7 torr for approximately 150 seconds. Sterilization chamber (152) may then be briefly vented (block 518) again to achieve a pressure level of approximately 30.1 torr, and then sterilization chamber (152) may be sealed (block 524) again. Sterilization chamber (152) may be held at the approximately 30.1 torr for approximately 200 seconds. Sterilization chamber (152) may then be briefly vented (block 518) again to achieve a pressure level of approximately 47.1 torr, and then sterilization chamber (152) may be sealed (block 524) again. Sterilization chamber (152) may be held at the approximately 47.1 torr for approximately 190 seconds. Sterilization chamber (152) may then be briefly vented (block 518) again to achieve a pressure level of approximately 760 torr (i.e., atmospheric pressure), thereby providing a diffusion phase. Of course, the foregoing is just one merely illustrative example.

In some variations, before the final step of venting (block 518) is reached, additional sterilant is introduced into sterilization chamber (152) during one or more of the acts of stepwise venting (block 518).

Also in some variations, a pre-plasma may be applied in the sterilization cycle (block 208) to heat up the medical device contained in sterilization chamber (152). By way of example only, plasma may be applied between applying a vacuum (block 510) and applying sterilant (block 514). In addition, or in the alternative, a post-plasma may be applied at the end of the sterilization cycle (block 208) to degrade any residual sterilant that may be adsorbed to the surface of the medical device contained in sterilization chamber (152). It should be understood that, before applying the post-plasma, a vacuum would first need to be applied to sterilization chamber (152).

As noted above, the sterilant is applied (block 514) in the form of a vapor within sterilization chamber (152). By way of example only, sterilization module (156) may comprise a combination of a vaporizer and a condenser. The vaporizer may include a chamber that receives a particular concentration of sterilant solution (e.g., a liquid hydrogen peroxide solution with a concentration of approximately 59% nominal, or between approximately 58% and approximately 59.6%); where the sterilant solution changes phase from liquid to vapor. The condenser may provide condensation of the sterilant solution vapor, and the concentration of the sterilant solution may be thereby increased (e.g., from approximately 59% nominal to somewhere between approximately 83% nominal and approximately 95% nominal), by removal of water vapor. Alternatively, any other suitable methods and components may be used to apply sterilant in the form of a vapor within sterilization chamber (152). In any case, to supplement the application of the sterilant in the form of a vapor, the sterilant may also be applied (in liquid form) to the inside of lumen(s) and/or other internal spaces within the medical device and/or the outside of the medical device, before the medical device is placed in sterilization chamber (152). In such versions, the sterilant may evaporate while vacuum is applied (block 510) and even after vacuum is applied (block 510); and provide more concentration of sterilant to the areas of the medical device with less penetration range, thereby further promoting effective sterilization.

By way of example only, the process depicted in FIG. 5 may be carried out at temperatures where the walls of sterilization chamber (152) are between approximately 30° C. and approximately 56° C., or more particularly between approximately 47° C. and approximately 56° C., or even more particularly approximately 50° C.; and where the temperature of the medical device in sterilization chamber (152) is between approximately 5-10° C. and approximately 40-55° C.

While the foregoing examples are described in the context of sterilizing medical devices, and particularly endoscopes, it should be understood that the teachings herein may also be readily applied in the context of sterilizing various other kinds of articles. The teachings are not limited to endoscopes or other medical devices. Other suitable articles that may be sterilized in accordance with the teachings herein will be apparent to those of ordinary skill in the art.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of sterilizing an article, the method comprising: (a) receiving the article in a sterilization chamber; (b) applying a vacuum to the sterilization chamber to reduce the pressure within the sterilization chamber to a first pressure, wherein the first pressure is less than atmospheric pressure; (c) introducing a sterilant into the sterilization chamber; (d) maintaining the first pressure in the sterilization chamber for a first period of time; (e) venting the sterilization chamber to increase the pressure within the sterilization chamber to a second pressure, wherein the second pressure is less than atmospheric pressure; (f) maintaining the second pressure in the sterilization chamber for a second period of time; (g) venting the sterilization chamber to increase the pressure within the sterilization chamber to a third pressure; and (h) maintaining the third pressure in the sterilization chamber for a third period of time.

Example 2

The method of Example 1, wherein the article comprises a medical device.

Example 3

The method of Example 2, wherein the medical device comprises an endoscope.

Example 4

The method of Example 3, wherein the endoscope defines a lumen.

Example 5

The method of Example 4, wherein the lumen has a length of at least 800 mm and an inner diameter less than 6 mm.

Example 6

The method of any one or more of Examples 1 through 5, wherein the second period of time is longer than the first period of time.

Example 7

The method of any one or more of Examples 1 through 6, wherein the first period of time is between approximately 5 seconds and approximately 5 minutes.

Example 8

The method of any one or more of Examples 1 through 7, wherein the first period of time is between approximately 20 seconds and approximately 2 minutes.

Example 9

The method of any one or more of Examples 1 through 8, wherein the second pressure is between approximately 10 torr greater than the first pressure and approximately 100 torr greater than the first pressure.

Example 10

The method of any one or more of Examples 1 through 9, wherein the second pressure is between approximately 10 torr greater than the first pressure and approximately 30 torr greater than the first pressure.

Example 11

The method of any one or more of Examples 1 through 10, wherein the third pressure is between approximately 10 torr greater than the second pressure and approximately 100 torr greater than the second pressure.

Example 12

The method of any one or more of Examples 1 through 11, wherein the third pressure is approximately 760 torr.

Example 13

The method of any one or more of Examples 1 through 12, further comprising applying a plasma to the sterilization chamber.

Example 14

The method of Example 13, wherein the act of applying a plasma comprises applying a plasma to the sterilization chamber between the act of applying the vacuum to the sterilization chamber and the act of introducing the sterilant to the sterilization chamber.

Example 15

The method of any one or more of Examples 13 through 14, wherein the act of applying a plasma comprises: (i) vacuuming the sterilization chamber after maintaining the third pressure in the sterilization chamber, and (ii) then applying a plasma.

Example 16

The method of any one or more of Examples 1 through 15, further comprising introducing additional sterilant into the sterilization chamber during the act of venting the sterilization chamber to increase the pressure within the sterilization chamber to the second pressure.

Example 17

The method of any one or more of Examples 1 through 16, further comprising applying sterilant to one or more internal spaces within the article before receiving the article in a sterilization chamber.

Example 18

The method of any one or more of Examples 1 through 17, wherein the sterilant is selected from the group consisting of hydrogen peroxide, peroxy acids, ozone, or a mixture thereof.

Example 19

A method of sterilizing an article, the method comprising: (a) receiving the article in a sterilization chamber; (h) applying a vacuum to the sterilization chamber to reduce the pressure within the sterilization chamber below atmospheric pressure; (c) introducing a sterilant into the sterilization chamber; (d) venting the sterilization chamber to incrementally increase the pressure within the sterilization chamber, without reaching atmospheric pressure; (e) maintaining the incrementally increased pressure in the sterilization chamber for a period of time; (f) repeating steps (d) through (e) at least once; (g) venting the sterilization chamber to increase the pressure within the sterilization chamber to atmospheric pressure.

Example 20

An apparatus, comprising: (a) a sterilization chamber, wherein the sterilization chamber is configured to receive a medical device; (b) a vacuum source in fluid communication with the sterilization chamber; (c) a sterilant applying module in fluid communication with the sterilization chamber; (d) a venting valve in fluid communication with the sterilization chamber, wherein the venting valve is further in fluid communication with atmosphere such that the venting valve is operable to selectively open and close a vent path between the sterilization chamber and atmosphere; and (e) a control module in communication with the vacuum source, wherein the control module is further in communication with the sterilant applying module, wherein the control module is further in communication with the venting valve, wherein the control module contains a control logic configured to execute a sterilizing algorithm such that the control logic is configured to: (i) activate the vacuum source to apply a vacuum to the sterilization chamber, (ii) activate the sterilant applying module to apply sterilant to the sterilization chamber, and (iii) selectively activate the venting valve to provide a step-wise incremental increase in pressure within sterilization chamber toward atmospheric pressure.

V. MISCELLANEOUS

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of sterilizing an endoscope, the method comprising:
   (a) receiving the endoscope in a sterilization chamber;
   (b) applying a vacuum to the sterilization chamber to reduce pressure within the sterilization chamber to a first pressure, wherein the first pressure is less than approximately 100 torr;
   (c) introducing a sterilant into the sterilization chamber;
   (d) maintaining the first pressure in the sterilization chamber for a first period of time;
   (e) after introducing the sterilant of step (c) and after maintaining the first pressure in the sterilization chamber for the first period of time of step (d), venting the sterilization chamber to atmosphere to increase the pressure within the sterilization chamber to a second pressure, wherein the second pressure is greater than the first pressure but is still less than 100 torr;
   (f) maintaining the second pressure in the sterilization chamber for a second period of time;
   (g) venting the sterilization chamber to atmosphere to increase the pressure within the sterilization chamber to a third pressure, wherein the third pressure is greater than the second pressure but is still less than 100 torr;
   (h) maintaining the third pressure in the sterilization chamber for a third period of time; and
   (i) venting the sterilization chamber to increase the pressure within the sterilization chamber to atmospheric pressure.

2. The method of claim 1, further comprising repeating steps (b) through (f) at least once.

3. The method of claim 1, further comprising repeating steps (b) through (f) at least twice.

4. The method of claim 1, further comprising repeating steps (g) through (h) at least once.

5. The method of claim 1, further comprising repeating steps (g) through (h) at least twice.

6. The method of claim 1, further comprising applying a plasma to the sterilization chamber between the step (b) of applying the vacuum to the sterilization chamber and the step (c) of introducing the sterilant to the sterilization chamber.

7. The method of claim 6, further comprising applying a vacuum to the sterilization chamber to reduce the pressure within the sterilization chamber then applying additional plasma to the sterilization chamber after step (i) of venting the sterilization chamber.

8. The method of claim 7, further comprising venting the sterilization chamber to a pressure of between 10 torr and the atmospheric pressure after applying the additional plasma to the sterilization chamber.

9. The method of claim 1, wherein the second pressure is approximately 10 torr to approximately 30 torr greater than the first pressure.

10. The method of claim 1, wherein the second pressure is not dependent on a temperature of the sterilization chamber.

11. The method of claim 1, wherein the second period of time is shorter or longer than the first period of time.

12. The method of claim 1, further comprising introducing additional sterilant into the sterilization chamber during the step (e) of venting the sterilization chamber to atmosphere to increase the pressure within the sterilization chamber to the second pressure or during the step (g) of venting the sterilization chamber to atmosphere to increase the pressure within the sterilization chamber to the third pressure.

13. The method of claim 1, further comprising applying liquid sterilant to one or more internal spaces within the endoscope before the step (a) of receiving the endoscope in the sterilization chamber.

14. The method of claim 1, wherein the sterilant is selected from the group consisting of hydrogen peroxide, peroxy acid, chlorine dioxide, or nitrogen dioxide.

15. The method of claim 1, wherein each of steps (b) through (i) are controlled automatically using a controller that includes a processor and memory.

16. The method of claim 1, further comprising monitoring a level of moisture within the sterilization chamber while reducing the level of moisture within the sterilization chamber until a predetermined level of moisture has been reached.

17. The method of claim 1, wherein the first pressure is approximately 0.2 torr and approximately 10 torr.

18. The method of claim 1, wherein the sterilant is hydrogen peroxide.

19. A method of sterilizing an endoscope, the method comprising:
   (a) receiving the endoscope in a sterilization chamber;
   (b) applying a vacuum to the sterilization chamber to reduce pressure within the sterilization chamber to a first pressure, wherein the first pressure is less than approximately 100 torr;
   (c) introducing a sterilant into the sterilization chamber;
   (d) maintaining the first pressure in the sterilization chamber for a first period of time;
   (e) after introducing the sterilant of step (c) and after maintaining the first pressure in the sterilization chamber for the first period of time of step (d), venting the sterilization chamber to atmosphere to increase the pressure within the sterilization chamber to a second pressure, wherein the second pressure is between 10 torr and approximately 30 torr greater than the first pressure but is still less than approximately 100 torr;
   (f) maintaining the second pressure in the sterilization chamber for a second period of time;
   (g) venting the sterilization chamber to increase the pressure within the sterilization chamber to a third pressure, wherein the third pressure is greater than the second pressure but is still less than approximately 100 torr;

(h) maintaining the third pressure in the sterilization chamber for a third period of time; and (i) venting the sterilization chamber to increase the pressure within the sterilization chamber to atmospheric pressure.

20. The method of claim 19, wherein the second period of time is shorter or longer than the first period of time.

21. The method of claim 19, further comprising repeating steps (b) through (f) at least once.

22. The method of claim 19, further comprising repeating steps (g) through (h) at least once.

23. The method of claim 1, wherein the sterilant is hydrogen peroxide.

24. A method of sterilizing an endoscope, the method comprising:

(a) receiving the endoscope in a sterilization chamber;

(b) applying a vacuum to the sterilization chamber to reduce pressure within the sterilization chamber to a first pressure, wherein the first pressure is less than 100 torr;

(c) introducing a sterilant into the sterilization chamber;

(d) maintaining the first pressure in the sterilization chamber for a first period of time;

(e) after introducing the sterilant of step (c) and after maintaining the first pressure in the sterilization chamber for the first period of time of step (d), venting the sterilization chamber to atmosphere to increase the pressure within the sterilization chamber to a second pressure, wherein the second pressure is greater than the first pressure but is still less than 100 torr;

(f) maintaining the second pressure in the sterilization chamber for a second period of time;

(g) venting the sterilization chamber to atmosphere to increase the pressure within the sterilization chamber to a third pressure, wherein the third pressure is greater than the second pressure but is still less than 100 torr;

(h) maintaining the third pressure in the sterilization chamber for a third period of time;

(i) applying the vacuum to the sterilization chamber to reduce the pressure within the sterilization chamber to a fourth pressure, wherein the fourth pressure is less than 100 torr;

(j) introducing additional sterilant gas into the sterilization chamber;

(k) maintaining the fourth pressure in the sterilization chamber for a fourth period of time; and (l) venting the sterilization chamber to increase the pressure within the sterilization chamber to a fifth pressure.

25. The method of claim 24, wherein the endoscope is between 1 meter and 3 meters in length and includes a lumen having a diameter of between 0.5 millimeters and 6 millimeters.

26. The method of claim 24, wherein the second pressure is approximately 10 torr to approximately 30 torr greater than the first pressure.

27. The method of claim 24, wherein the fifth pressure is the atmospheric pressure.

28. The method of claim 24, wherein the fifth pressure is greater than the fourth pressure but is less than 100 torr.

29. The method of claim 24, further comprising applying plasma between the step (b) of applying the vacuum to the sterilization chamber and the step (c) of introducing the sterilant to the sterilization chamber.

30. The method of claim 24, wherein the second pressure is approximately 10 torr to approximately 30 torr greater than the first pressure.

31. The method of claim 24, wherein the first pressure is between approximately 0.2 torr and approximately 10 torr.

* * * * *